US00PP12574P2

(12) United States Plant Patent

Yates

(10) Patent No.: US PP12,574 P2
(45) Date of Patent: Apr. 23, 2002

(54) JAMESBRITTENIA PLANT NAMED 'YAGERO'

(76) Inventor: Frederic Yates, Poplar Nursery, Holmes Chapel Rd., Somerford, Congleton, Cheshire (GB), CW12 4FP ( * ) Notice: Subject to any disclaimer, the term of this patent is extended or adjusted under 35 U.S.C. 154(b) by 0 days.

(21) Appl. No.: 09/689,332

(22) Filed: Oct. 12, 2000

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Susan B. McCormick
(74) *Attorney, Agent, or Firm*—Mark P. Bourgeois

(57) ABSTRACT

A new cultivar of Jamesbrittenia plant named 'Yagero', that is characterized by its unique smaller leaf size, marginally lobed leaf shape, and rose-colored flowers, setting it apart from all existing commercial varieties known to the inventor.

2 Drawing Sheets

CROSS-REFERENCES TO RELATED APPLICATIONS

This application corresponds to two other applications entitled Jamesbrittenia Plant Named 'Yagevi' (U.S. patent application Ser. No. 09/689,324) and Jamesbrittenia Plant Named 'Yagepin' (U.S. patent application Ser. No. 09/689,327), both of which have the same inventor and filing date as the present invention.

BACKGROUND OF THE INVENTION

The present invention relates to a new and distinct cultivar known botanically as a Jamesbrittenia of hybrid origin and referred to hereinafter by the cultivar name 'Yagero'. The genus Jamesbrittenia has been split from the genus Sutera under which plants of Jamesbrittenia have hitherto been classified.

The new cultivar was bred and selected from a long term breeding program aimed at producing new forms and colors of patio plants and hanging baskets. The exact parents of 'Yagero' are unidentified Jamesbrittenia species hybrids. The original breeding material included Jamesbrittenia species *jurassica, breviflora, microphylla* and *pristisepala* (none of these have been patented). Through open pollination the species hybridized producing many generations of seedlings. From these seedlings that resulted from various unidentified crosses of Jamesbrittenia species, four new selections were made. The program was conducted by the inventor in a cultivated area of Congleton, Chesire England. The inventor conducted first crosses in the summer of 1992 and made four selections in 1999, of which 'Yagero' was one. The method of origination or breeding technique was seedling selection and re-selection, followed by asexual propagation using cuttings.

'Yagero' was selected for its characteristics as a new hanging basket and can be distinguished as unique because of its leaf size, leaf shape and its flower color. Compared to other varieties existing in the trade, 'Yagero' has smaller leaves. Although 'Yagero' resembles 'Yagepin' and 'Yagevi' in its small marginally lobed foliage, it differs in flower color from the other two. 'Yagero' exhibits rose-colored flowers while 'Yagevi' exhibits violet-colored flowers and 'Yagepin' has pink-colored flowers.

The first asexual propagation was conducted by the inventor in Congleton, Chesire England in 1999. The new individual has been found to be stable through many cycles of vegetative propagation.

SUMMARY OF THE INVENTION

The following traits have been repeatedly observed and represent the characteristics of the new cultivar. These attributes in combination distinguish this cultivar from all other varieties known to the inventor. 'Yagero' is a new selection for a hanging basket, distinguished by its leaf size and shape, and flower color. The foliage is similar to 'Yagepin' and 'Yagevi' however, the leaves are smaller and marginally lobed in comparison to other existing varieties in the trade. Rose-colored flowers distinguish 'Yagero' from the two co-pending varieties, 'Yagevi' and 'Yagepin'.

BRIEF DESCRIPTION OF THE DRAWINGS

The accompanying color photographs illustrate the overall appearance of the new cultivar.

The photo on sheet 1 is a good representation of the plant form, foliage, and flower color.

The photo on sheet 2 is a close-up comparison of the flowers, 'Yagero' on the right and 'Yagepin' on the left. All photographs are taken of plants grown in one-gallon containers. The prints are made using conventional photographic techniques and although colors in photographs may appear different from actual colors due to light reflectance they are as accurate as possible by conventional photography.

BOTANICAL DESCRIPTION OF THE PLANT

The following is a detailed description of the new cultivar as grown in a one-gallon container under greenhouse conditions in Encinitas, Calif. Phenotypic differences may be observed with variations in environmental, climatic and cultural conditions. The color determinations are in accordance with The Royal Horticultural Society Colour Chart except where general color terms of ordinary dictionary significance are used.

Botanical classification: Jamesbrittenia 'Yagero'.
Common name: Bacopa.

Use: Hanging basket, patio plant.
Parentage: The parents of 'Yagero' are Jamesbrittenia species hybrids.
*Seed parent.*—Unidentified Jamesbrittenia species hybrid.
*Pollen parent.*—Unidentified Jamesbrittenia species hybrid.
Propagation: Vegetative cuttings.
Type: Annual patio container or hanging basket.
Seasonal interest: Profuse floral display.
Cropping time: 8 weeks to root from a cutting.
Root system: Fibrous.
Special growing requirements: Shear after heavy flowering.
Diseases and pests: Potential for mildew.
Growth habit: Trailing and cascading.
Height: 35 cm. high.
Width: 60 cm. wide.
Hardiness: Observed as hardy from −5 to 10 degrees Centigrade, however hardiness has not been fully tested.
Soil: Free-draining.
Light levels: Plant in part shade to full sun.
Stem shape: Cylindrical.
Stem color: 144C.
Stem size: 20–28 cm. long by 2 mm. wide.
Internode length: 1 to 1.5 cm. between nodes.
Stem surface: Pubescent with short hairs.
Foliage:
*Leaf arrangement.*—Opposite.
*Leaf division.*—Simple.
*Shape.*—Lyrate with shallow terminal lobes.
*Base.*—Acuminate.
*Apex.*—Retuse with two notches.
*Venation.*—Prominent mid-vein.
*Margins.*—Pinnately lobed.
*Surface* (*upper and lower*).—Pubescent.
*Length.*—1 cm. long.
*Width.*—1 cm. wide.
*Color upper surface.*—138A.
*Color lower surface.*—139C.
*Petiole.*—1 mm. wide and 4 mm. long.
Flower:
*Type.*—Solitary.
*Shape.*—Circular, rotate.
*Form.*—Corymb.
*Margins.*—Entire.
*Texture.*—Glabrous.
*Fragrance.*—None observed.
*Flower size.*—1.5 cm. wide by 1.5–2 cm. high.
*Flowering season.*—Spring and summer.
*Flowering time.*—Diurnal.
*Aspect.*—Facing upward and outward.
*Peduncle length.*—4 to 5 mm. long.
*Peduncle width.*—1 mm. wide.
*Peduncle color.*—138B.
*Persistent or non-persistent.*—Persistent.
*Petals.*—Five petals.
*Fused or unfused.*—Petals are fused at base.
*Petal color.*—Overall color is 74A with 81A partially surrounding throat entrance.
*Throat markings.*—2C, 155D.
*Calyx size.*—3 mm. long by 2.5 mm. wide.
*Calyx color.*—144B.
*Sepal color.*—144B.
*Sepal width and length.*—3 mm. wide by 2.5 mm. long.
*Sepal number.*—Five sepals.
Reproductive organs:
*Stamens.*—Two stamens.
*Stamen dimensions.*—6–7 mm. in length and 0.50 mm. in diameter.
*Pollen color.*—25A.
*Pistil color.*—144C.
*Number of pistils.*—One in number.
*Pistil dimensions.*—6.5–7.5 mm. in length and 0.75 mm. in diameter.
Seed production:
*Seed shape.*—Spherical in shape.
*Seed dimensions.*—0.60–0.75 mm. in diameter and 0.60–0.75 mm. in height.
*Seed color.*—199B.
*Capsule color.*—200A.
*Capsule dimensions.*—2.5 mm. in diameter and 6 mm. in length.
*Capsule shape.*—Ovate.
*Seed surface.*—Glabrous.
*Seed quantity.*—30–40 per capsule.

I claim:

1. A new and distinct cultivar of Jamesbrittenia plant named 'Yagero' as described and illustrated.

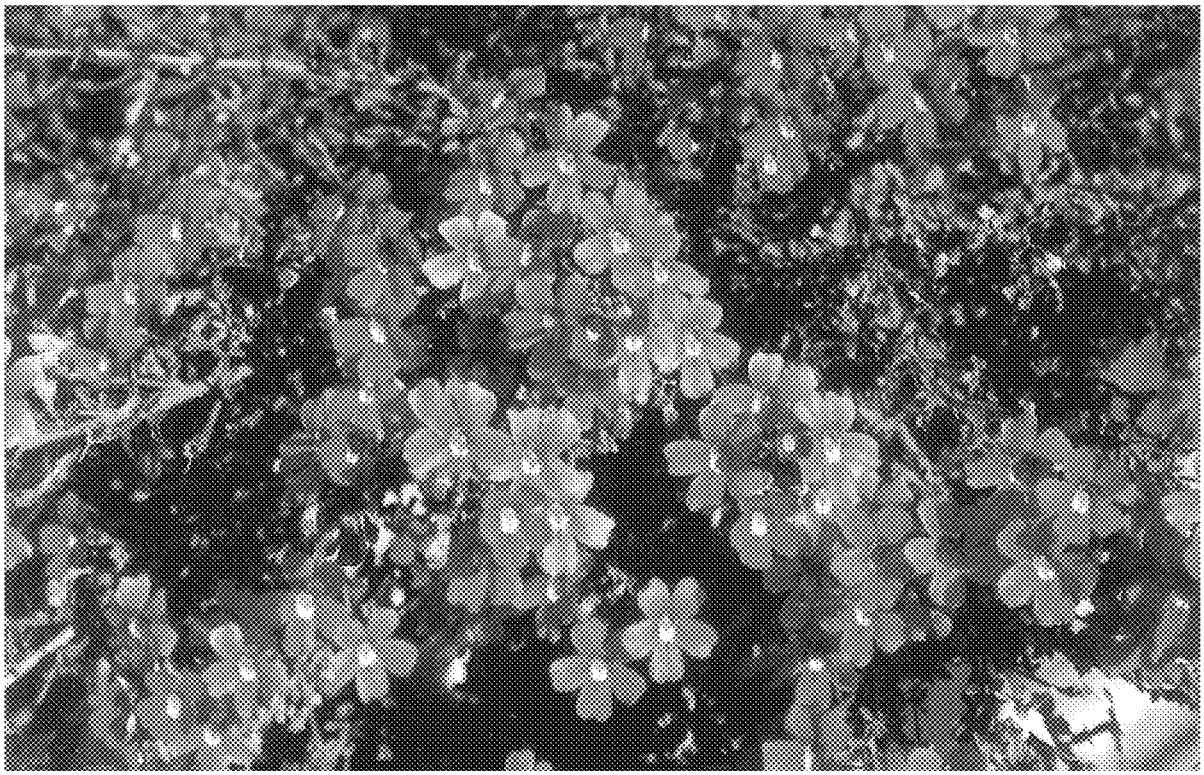

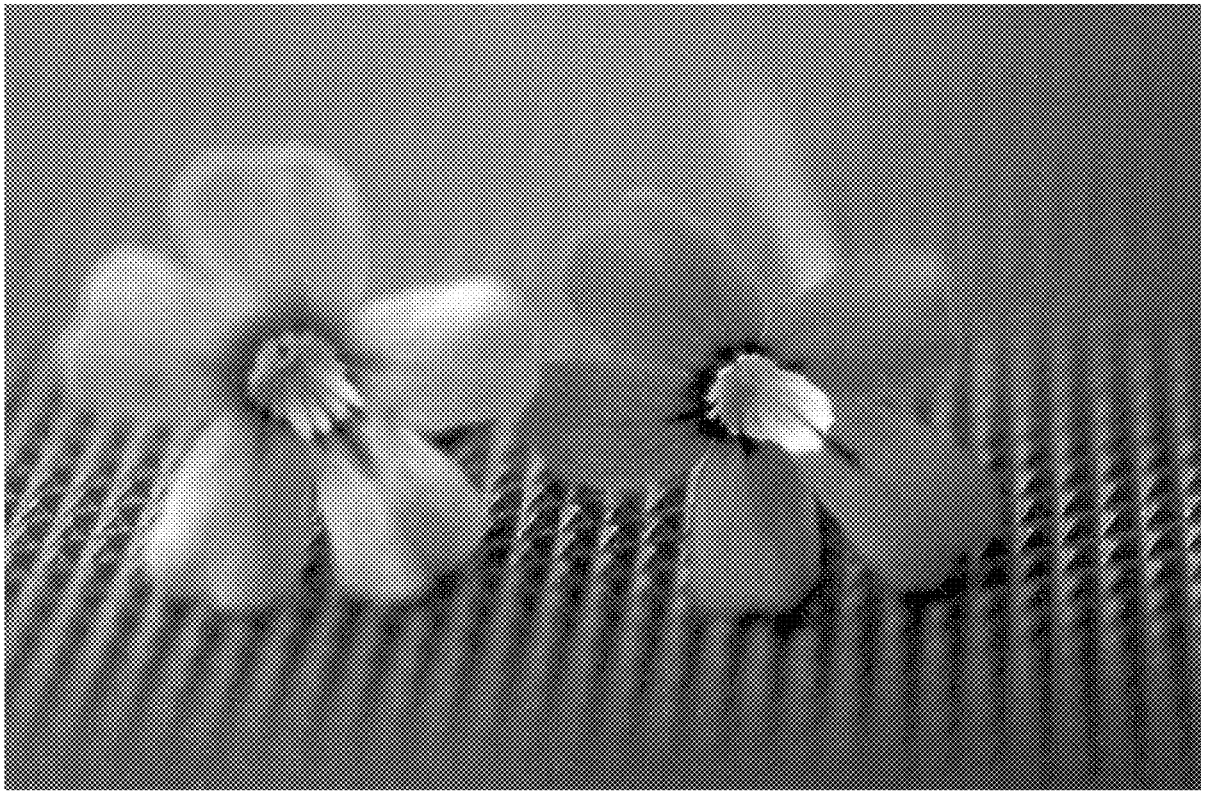

* * * * *